United States Patent [19]
Hu

[11] Patent Number: 5,260,300
[45] Date of Patent: Nov. 9, 1993

[54] RAPAMYCIN CARBONATE ESTERS AS IMMUNO-SUPPRESSANT AGENTS

[75] Inventor: David C. Hu, Highland Park, N.J.

[73] Assignee: American Home Products Corporation, New York, N.Y.

[21] Appl. No.: 979,072

[22] Filed: Nov. 19, 1992

[51] Int. Cl.$^5$ .................. A61K 31/395; C07D 491/06
[52] U.S. Cl. ........................ 514/291; 546/90; 540/456; 540/452
[58] Field of Search ................... 546/90; 540/456

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit | 546/90 |
| 4,401,653 | 8/1983 | Eng | 424/114 |
| 4,650,803 | 3/1987 | Stella et al. | 546/90 |
| 4,885,171 | 12/1989 | Surendra et al. | 424/122 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,899 | 3/1992 | Calne | 514/291 |
| 5,118,678 | 6/1992 | Kao et al. | 514/183 |

OTHER PUBLICATIONS

Martel, et al., Can. J. Physiol. Pharm. 55, 48–51, (1977).
Calne, et al., The Lancet, Jun. 3, 1978, pp.
Dumont et al., FASEB 3(4), 5256 (1989).
Staruch et al., FASEB 3(3), 3411 (1989).
Vezina et al., Journal of Antibiotics 28(10), 721–26 (1975).
Sehgal et al., Journal of Antibiotics 28(10), 727–32 (1975).
Baker et al., Journal of Antibiotics 31(6), 539–545 (1978).
Fieser and Fieser, Reagents for Organic Synthesis, vol. I p. 364, 366 Wiley 1967.

Primary Examiner—Mukund J. Shah
Assistant Examiner—Pavanaram K. Sripada
Attorney, Agent, or Firm—R. F. Boswell, Jr.

[57] ABSTRACT

Carbonate esters with rapamycin at position 42 or positions 31 and 42 have been shown to have immunosuppressant properties and are useful in the treatment of transplant rejections and autoimmune diseases. These esters are represented by the formula below:

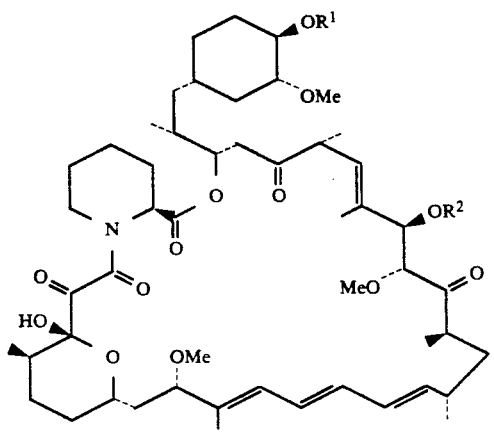

wherein:
R$^1$ and R$^2$ are independently H or —COOR$^3$ but both R$^1$ and R$^2$ cannot be H, and
R$^3$ is C$_1$-C$_6$ alkyl where 1 to 3 hydrogens may be replaced by fluorine, chlorine, bromine or iodine, C$_3$-C$_8$ cycloalkyl, C$_2$-C$_6$ alkenyl, or Ar—(CH$_2$)$_n$— where n is 0 to 6 and Ar is phenyl, phenyl substituted by fluorine, chlorine, bromine, iodine, trifluoromethyl, nitro, cyano, C$_1$-C$_6$ alkyl or C$_1$-C$_6$ alkoxy; pyridinyl, indolyl, quinolyl or furanyl;
or a pharmaceutically acceptable salt thereof.

13 Claims, No Drawings

RAPAMYCIN CARBONATE ESTERS AS IMMUNO-SUPPRESSANT AGENTS

FIELD OF THE INVENTION

This invention relates to novel carbonate esters of rapamycin, their use in methods of treatment, and pharmaceutical compositions thereof.

BACKGROUND OF THE INVENTION

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al, J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al., [Can. J. Physiol. Pharmacol. 55,48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin has been shown to be effective in inhibiting transplant rejection (U.S. Pat. No. 5,100,899). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

U.S. Pat. No. 5,080,899 discloses a method of treating pulmonary inflammation with rapamycin. U.S. Pat. No. 5,078,999 discloses a method of treating systemic lupus erythematosus with rapamycin.

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. Immunosuppressive, antifungal, and antitumor activities of rapamycin 31 and/or 42 carbamate esters are disclosed in U.S. Pat. No. 5,118,678.

SUMMARY OF THE INVENTION

The novel carbonate derivatives of rapamycin have the structure shown in Formula I below.

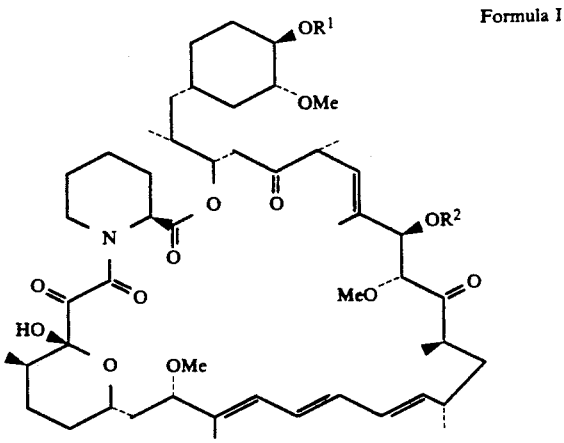

Formula I

Under Formula I, $R^1$ and $R^2$ are independently H or —$COOR^3$ but both $R^1$ and $R^2$ cannot be H at the same time. $R^3$ is selected from $C_1$–$C_6$ alkyl where 1 to 3 hydrogens may be replaced by fluorine, chlorine, bromine or iodine, $C_3$–$C_8$ cycloalkyl, $C_2$–$C_6$ alkenyl or Ar—$(CH_2)_n$—where n is 0–6 and Ar is phenyl, phenyl substituted by fluorine, chlorine, bromine, iodine, trifluoromethyl, nitro, cyano, $C_1$–$C_6$ alkyl or $C_1$–$C_6$ alkoxy; pyridinyl, indolyl, quinolyl or furanyl. Formula I also encompasses the pharmaceutically acceptable salts which includes hydrates, solvates, and acid addition salts when they can be formed.

Immunosuppressive activity was determined in an in vitro standard pharmacological test to measure lymphocyte proliferation (LAF). In this in vitro test, rapamycin itself has an $IC_{50}$ of 1.7–6.3 nM and the carbonate esters of this invention have $IC_{50}$'s ranging from 0.32 to 2.5 nM. Thus in this assay, the invention compounds have LAF activity equal or greater than rapamycin and would therefore be expected to posses the immunological properties of rapamycin and be useful in the treatment of transplantation rejection and autoimmune diseases such as lupus, rheumatoid arthritis, diabetes mellitus, multiple sclerosis, psoriasis and the like. Because of the structural similarity of the invention compounds with rapamycin and other analogs having antifungal activity against several strains of *Candida albicans*, the compounds of this invention would also be expected to have antifungal properties. Similarly, the compounds of this invention would be expected to have antiinflammatory activity.

DETAILED DESCRIPTION OF THE INVENTION

The invention compounds are prepared by dissolving rapamycin in a mixture of ether and tetrahydrofuran (THF) and treating with 3 equivalents of pyridine. The mixture is cooled to 0° C. and treated with a chloroformate (3 equivalents) of the formula $ClCO_2R^3$ where $R^3$ is as defined under Formula I. After a suitable period of time, the reaction is quenched with dilute acid and the isolated mixture of carbonate esters and starting materials subjected to flash chromatography on silica gel to obtain the desired carbonate esters. The position 42 carbonate esters are the major reaction product. The 31, 42-dicarbonate esters, and 31-carbonate esters, when isolated, are obtained as a minor product.

Specific examples of the synthetic procedures follow. These examples are given for illustrative purposes only and are not to be construed as limiting to this disclosure which is limited only by the scope of the appended claims.

EXAMPLE 1

(A) 31, 42-O-Bis(methoxycarbonyl)rapamycin (B) 42-O-Methoxycarbonylrapamycin

To a solution of rapamycin (0.83 g, 0.908 mmol) in ether/THF (30 mL, ether:THF=2:1) in a 250 mL flask equipped with a magnetic stirrer under nitrogen at room temperature is added pyridine (0.25 mL, 3.09 mmol) dropwise. The solution is cooled to 0° C. and stirred for 30 minutes. To the solution is added methyl chloroformate (0.22 mL, 2.85 mmol) dropwise over a period of ten minutes. The reaction mixture is stirred at 0° C. for thirty minutes, warmed to room temperature, and stirred for 24 hours.

The reaction is quenched with approximately 50 mL of 1N HCl. The organic layer is separated, and the aqueous layer is extracted three times with ether followed by three times with ethyl acetate. The combined organic layers are washed with brine and dried over $Na_2SO_4$. The solution is filtered and concentrated in vacuo to afford a pale yellow powder (0.88 g). Analysis by analytical TLC indicated at least three compounds are present in the reaction mixture.

The reaction mixture is dissolved in EtOAc (20 mL) and the compounds separated by flash chromatography (silica gel on a 50 mm column, 50% EtOAc-hexane gradient to 100% EtOAc). Two compounds (A and B) are separated and the fractions concentrated in vacuo. Analysis of compound A (0.0143 g, 15% overall yield) indicated that it is 31, 42-O-bis(methoxycarbonyl)-rapamycin.

$^1$H NMR (400 MHz, $CDCl_3$): δ5.2 (d, 1H), 4.5-4.55 (m, 1H), 3.8 (s, 3H), 3.7 (s, 3H).

MS (neg. ion FAB) m/e: 1029 (M$^-$), 997, 952, 590, 379.

Compound B (0.5725 g, 65% overall yield) is 42-O-methoxycarbonyl-rapamycin.

$^1$H NMR (400 MHz, $CDCl_3$): δ4.5-4.58 (m, 1H), 3.79 (s, 3H).

MS (neg. ion FAB) m/e: 971 (M$^-$), 590, 379.

IR (KBr, cm$^{-1}$): 3400, 2950, 1750, 1645, 1440.

Anal. calcd. for $C_{53}H_{81}NO_{15}.H_2O$: C 64.30%, H 8.29%, N 1.42%; Found: C 64.08%, H 8.13%, N 1.35%.

EXAMPLE 2.

(A) 31, 42-O-Bis(ethoxycarbonyl)rapamycin (B) 42-O-Ethoxycarbonylrapamycin

To a solution of rapamycin (0.53 g, 0.580 mmol) in ether/THF (40 mL, ether:THF=1:1) in a 250 mL flask equipped with a magnetic stirrer under nitrogen at room temperature is added pyridine (0.15 mL, 1.85 mmol) dropwise. The solution is cooled to 0° C. and stirred for 30 minutes. To the solution is added ethyl chloroformate (0.17 mL, 1.78 mmol) dropwise over a period of ten minutes. The reaction mixture is stirred at 0° C. for thirty minutes, warmed to room temperature, and stirred for 24 hours.

The reaction is quenched with approximately 50 mL of 1N HCl. The organic layer is separated, and the aqueous layer is extracted three times with ether followed by three times with ethyl acetate. The combined organic layers are washed with brine and dried over $Na_2SO_4$. The solution is filtered and concentrated in vacuo to afford a pale yellow powder (0.38 g). Analysis by analytical TLC indicated at least three compounds are present in the reaction mixture.

The reaction mixture is dissolved in EtOAc (15 mL) and the compounds separated by flash chromatography (silica gel on a 50 mm column, 50% EtOAc-hexane gradient to 100% EtOAc). Two compounds (A and B) are separated and the fractions concentrated in vacuo. Analysis of compound A (0.011 g, 1.8% overall yield) indicated that it is 31, 42-O-bis(ethoxycarbonyl)-rapamycin.

$^1$H NMR (400 MHz, $CDCl_3$): δ5.38 (d, 1H), 4.5-4.58 (m, 1H), 4.2 (q, 2H), 4.15 (q, 2H), 1.3 (t, 3H), 1.25 (t, 3H).

MS (neg. ion FAB) m/e: 1057 (M$^-$), 590, 393.

IR (KBr, cm$^{-1}$): 3400, 2910, 1735, 1640, 1450.

Anal. calcd. for $C_{57}H_{87}NO_{17}$: C 64.69%, H 8.29%, N 1.32%; Found: C 64.63%, H 8.19%, N 1.20%.

Compound B (0.3054 g, 53% overall yield) is 42-O-ethoxycarbonyl-rapamycin.

$^1$H NMR: δ4.55-4.6 (m, 1H), 4.2 (q, 2H), 1.2 (t, 3H).

MS (neg. ion FAB) m/e: 985 (M$^-$), 590, 393.

IR (KBr, cm$^{-1}$): 3430, 2910, 1740, 1640, 1450.

EXAMPLE 3

42-O-(Phenyloxycarbonyl)rapamycin.

To a solution of rapamycin (1.05 g, 1.148 mmol) in ether/THF (30 mL, ether:THF=1:1) in a 250 mL flask equipped with a magnetic stirrer under nitrogen at room temperature is added pyridine (0.30 mL, 3.71 mmol) dropwise. The solution is cooled to 0° C. and stirred for 30 minutes. To the solution is added phenyl chloroformate (0.50 mL, 3.99 mmol) dropwise over a period of twelve minutes. The reaction mixture is stirred at 0° C. for thirty minutes, warmed to room temperature, and stirred for three hours.

The reaction is quenched with approximately 50 mL of 1N HCl. The organic layer is separated, and the aqueous layer is extracted with ether followed by ethyl acetate. The combined organic layers are washed with brine and dried over $Na_2SO_4$. The solution is filtered and concentrated in vacuo to afford a pale yellow powder (0.84 g). Analysis by analytical TLC indicated at least two compounds are present in the reaction mixture.

The reaction mixture is dissolved in EtOAc (15 mL) and the compounds separated by flash chromatography (silica gel on a 50 mm column, 75% EtOAc-hexane gradient to 100% EtOAc). The fraction containing the major product is concentrated in vacuo to afford a pale yellow foam (0.53 g, 47% overall yield). Analysis indicated that the compound isolated is the monohydrate of 42-O-(phenyloxycarbonyl)-rapamycin.

$^1$H NMR (400 MHz, $CDCl_3$): δ7.18-7.4 (m, 5H), 4.5-4.62 (m, 1H).

MS (neg. ion FAB) m/e: 971 (M$^-$), 590,441.

IR (KBr, cm$^{-1}$): 3450, 2930, 1720, 1640, 1460.

Anal. calcd. for $C_{58}H_{83}NO_{15}.H_2O$: C 67.35%, H 8.09%, N 1.35%;

Found: C 64.88%, H 7.76%, N 1.29%.

EXAMPLE 4

A. 42-O-(4-Nitrophenyloxycarbonyl)rapamycin

To a solution of rapamycin (1.13 g, 1.240 mmol) in ether/THF (30 mL, ether:THF=1:1) in a 250 mL flask equipped with a magnetic stirrer under nitrogen at room temperature is added pyridine (0.30 mL, 3.71 mmol) dropwise. The solution is cooled to 0° C. and stirred for 30 minutes. To the solution is added 4-nitrophenyl chloroformate (0.748 g, 3.71 mmol) portionwise over a period of five minutes. The reaction mixture is stirred at 0° C. for thirty minutes.

The reaction is quenched with approximately 50 mL of 1N HCl. The organic layer is separated, and the aqueous layer is extracted with ether followed by ethyl acetate. The combined organic layers are washed with brine and dried over $Na_2SO_4$. The solution is filtered and concentrated in vacuo to afford a pale yellow powder (1.05 g). Analysis by analytical TLC indicated at least two compounds are present in the reaction mixture.

The reaction mixture is dissolved in EtOAc (15 mL) and the compounds separated by flash chromatography (silica gel on a 50 mm column, 50% EtOAc-hexane gradient to 100% EtOAc). The fraction containing the major product is concentrated in vacuo to afford a pale yellow foam (0.58 g, 43% overall yield). Analysis indicated that it is 42-O-(4-nitro-phenyloxycarbonyl)-rapamycin.

$^1$H NMR (400 MHz, DMSO): δ8.2 (d, 2H), 7.4 (d, 2H), 4.5–4.58 (m, 1H).

MS (neg. ion FAB) m/e: 1078 (M−), 590, 138.

IR (KBr, cm$^{-1}$): 3430, 2930, 1760, 1730, 1640, 1530, 1450.

B. 31, 42-O-Bis(4-Nitrophenyloxycarbonyl)rapamycin

To a solution of rapamycin (1.33 g, 1.46 mmol) in ether/THF (50 mL, ether:THF=1.1) in a 250 mL flask equipped with a magnetic stirrer under nitrogen at room temperature is added pyridine (0.36 mL, 4.452 mmol) dropwise. The solution is cooled to 0° C. and stirred for 30 minutes. To the solution is added 4-nitrophenyl chloroformate (0.8965 g, 4.45 mmol) portionwise over a period of five minutes. The reaction mixture is stirred at 0° C. for one hour.

The reaction is quenched with approximately 60 mL of 1N HCl. The organic layer is separated, and the aqueous layer is extracted with ether followed by ethyl acetate. The combined organic layers are washed with brine and dried over $Na_2SO_4$. The solution is filtered and concentrated in vacuo to afford a pale yellow powder (1.47 g). Analysis by analytical TLC indicated the presence of two components.

The reaction mixture is dissolved in EtOAc (21 mL) and the compounds separated by flash chromatography (silica gel on a 50 mm column, 60% EtOAc-hexane). The fraction containing the major component is concentrated in vacuo to afford a pale yellow foam (1.129 g, 62% overall yield). Analysis indicated that it is 31, 42-O-Bis(4-nitrophenyloxycarbonyl)rapamycin.

$^1$H NMR (400 MHz, DMSO): δ8.35 (dd, 4H), 7.52 (d, 2H), 7.45 (d, 2H), 4.58 (d, 1H), 4.35–4.42 (m, 1H).

MS (neg. ion FAB)m/e: 1243(M−), 1078, 590, 446, 138.

IR (KBr, cm$^{-1}$): 3430, 2930, 1760, 1730, 1640, 1530, 1450.

EXAMPLE 5

42-O-(Prop-2-enyloxycarbonyl)rapamycin

To a solution of rapamycin (1.17 g, 1.28 mmol) in ether/THF (30 mL, ether:THF=1.1) in a 250 mL flask equipped with a magnetic stirrer under nitrogen at room temperature is added pyridine (0.31 mL, 3.74 mmol) dropwise. The solution is cooled to 0° C. and stirred for 30 minutes. To the solution is added allyl chloroformate (0.41 mL, 3.86 mmol) dropwise over a period of ten minutes. The reaction mixture is stirred at 0° C. for thirty minutes, warmed to room temperature, and stirred for 36 hours.

The reaction is quenched with approximately 50 mL of 1N HCl. The organic layer is separated, and the aqueous layer is extracted with ether followed by ethyl acetate. The combined organic layers are washed with brine and dried over $Na_2SO_4$. The solution is filtered and concentrated in vacuo to afford a pale yellow powder (0.53 g). Analysis by analytical TLC indicated at least two compounds present in the reaction mixture.

The reaction mixture is dissolved in EtOAc (20 mL) and the compounds separated by flash chromatography (silica gel on a 50 mm column, 25% EtOAc-hexane gradient to 75% EtOAc). The fraction containing the major product is concentrated in vacuo to afford a pale yellow foam (0.18 g, 14% overall yield). Analysis indicated that the product isolated is the trihydrate of 42-O-(prop-2-enyloxycarbonyl)rapamycin.

$^1$H NMR (400 MHz, DMSO): δ5.85–5.95 (m, 1H), 5.2–5.35 (dd, 2H), 4.3–4.45 (m, 1H).

MS (neg. ion FAB) m/e: 971 (M−), 590, 405.

IR (KBr, cm$^{-1}$): 3420, 2910, 2370, 1740, 1640, 1450.

Anal. calcd. for $C_{55}H_{83}NO_{15} \cdot 3H_2O$: C 62.79%, H 8.06%, N 1.33%;

Found: C 62.43%, H 8.04%, N 1.34%.

EXAMPLE 6

42-O-(Benzyloxycarbonyl)rapamycin

To a solution of rapamycin (1.14 g, 1.25 mmol) in ether/THF (40 mL, ether:THF=1:1) in a 250 mL flask equipped with a magnetic stirrer under nitrogen at room temperature is added pyridine (0.30 mL, 3.71 mmol) dropwise. The solution is cooled to 0° C. and stirred for 30 minutes. To the solution is added benzylchloroformate (0.53 mL, 3.71 mmol) dropwise over a period of ten minutes. The reaction mixture is stirred at 0° C. for two hours, warmed to room temperature, and stirred for 30 hours.

The reaction is quenched with approximately 50 mL of 1N HCl. The organic layer is separated, and the aqueous layer is extracted with ether followed by ethyl acetate. The combined organic layers are washed with brine and dried over $Na_2SO_4$. The solution is filtered and concentrated in vacuo to afford a pale yellow powder (0.47 g). Analysis by analytical TLC indicated at least two compounds present in the reaction mixture.

The reaction mixture is dissolved in EtOAc (20 mL) and the compounds separated by flash chromatography (silica gel on a 50 mm column, 50% EtOAc-hexane). The fraction containing the major product is concentrated in vacuo to afford a pale yellow foam (0.310 g, 23% overall yield). Analysis indicated that it is 42-O-(benzyloxycarbonyl)rapamycin with 2.5 moles of water.

$^1$H NMR (400 MHz, DMSO): δ5.15 (s, 1H), 5.2–5.35 (dd, 2H), 4.35–4.42 (m, 1H).

MS (neg. ion FAB) m/e: 1047 (M−), 590, 455.

IR (KBr, cm$^{-1}$): 3440, 2920, 1740, 1640, 1450.

Anal. calcd. for $C_{59}H_{85}NO_{15} \cdot 2.5H_2O$: C 64.88%, H 8.24%, N 1.28%;

Found: C 64.82%, H 7.95%, N 1.13%.

EXAMPLE 7

Following the procedures outlined in Example 6 and substituting the following for benzylchloroformate:
 a. 4-fluorophenylchloroformate
 b. vinylchloroformate c. 2-trichloroethylchloroformate
d. 4-methoxyphenylchloroformate
e. allylchloroformate
f. 4-nitrobenzylchloroformate
g. 2-bromoethylchloroformate there are obtained respectively:
a. 42-O-(4-fluorophenyloxycarbonyl)rapamycin
b. 42-O-(vinyloxycarbonyl)rapamycin
c. 42-O-(2-trichloroethyloxycarbonyl)rapamycin
d. 42-O-(4-methoxyphenyloxycarbonyl)rapamycin
e. 42-O-(allyloxycarbonyl)rapamycin
f. 42-O-(4-nitrobenzyloxycarbonyl)rapamycin
g. 42-O-(2-bromoethyloxycarbonyl)rapamycin.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation at a concentration of 1 $\mu$M or as the IC$_{50}$.

$$\frac{^3\text{H-control thymus cells} - {}^3\text{H-rapamycin-treated thymus cells}}{^3\text{H-control thymus cells} - {}^3\text{H-test compound-treated cells}}$$

The pharmacological data obtained in the above tests with the invention compounds is shown in Table I along with comparative results with rapamycin.

TABLE I

| | IC$_{50}$ DATA FOR LAF ASSAY | | | | |
|---|---|---|---|---|---|
| | IC$_{50}$ | | | IC$_{50}$ | |
| Example | Ester | Rapamycin | Example | Ester | Rapamycin |
| 1A | 0.87 | 2.7 | 4A | 1.00 | 6.3 |
| 1B | 2.50 | 3.9 | 4B | 23 | 1.6 |
| 2A | 2.00 | 3.9 | 5 | 1.60 | 3.8 |
| 2B | 0.60 | 3.9 | 6 | 0.32 | 3.8 |
| 3 | 0.34 | 6.3 | | | |

PHARMACEUTICAL COMPOSITION

The compounds can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–5 percent, preferably 2%, of active compound which may be administered to a fungally affected area.

What is claimed is:

1. A compound according to the formula:

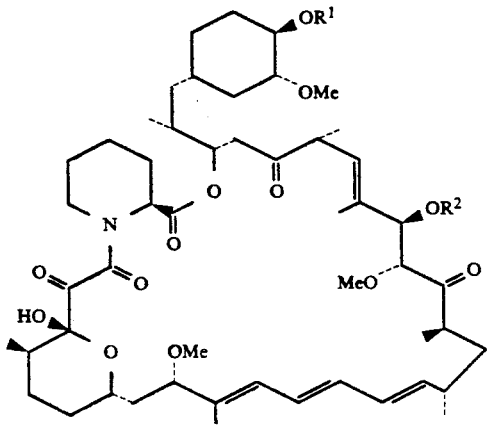

wherein:

R$^1$ and R$^2$ are independently H or —COOR$^3$ but both R$^1$ and R$^2$ cannot be H, and R$^3$ is C$_1$–C$_6$ alkyl where 1 to 3 hydrogens may be replaced by fluorine, chlorine, bromine or iodine, C$_3$–C$_8$ cycloalkyl, C$_2$–C$_6$ alkenyl, or Ar—(CH$_2$-)$_n$—where n is 0 to 6 and Ar is phenyl, phenyl substituted by fluorine, chlorine, bromine, iodine, trifluoromethyl, nitro, cyano, C$_1$–C$_6$ alkyl or C$_1$–C$_6$ alkoxy; pyridinyl, indolyl, quinolyl or furanyl;

or a pharmaceutically acceptable salt thereof.

2. A compound according to claim 1 which is 31,42-O-bis(methoxycarbonyl)-rapamycin.

3. A compound according to claim 1 which is 41-O-(methoxycarbonyl)rapamycin.

4. A compound according to claim 1 which is 31,42-O-bis(ethoxycarbonyl)rapamycin.

5. A compound according to claim 1 which is 42-O-(ethoxycarbonyl)rapamycin.

6. A compound according to claim 1 is 42-O-(phenyloxycarbonyl)rapamycin.

7. A compound according to claim 1 which is 42-O-(4-nitrophenyloxycarbonyl)-rapamycin.

8. A compound according to claim 1 which is 31,42-O-bis(4-nitrophenyloxycarbonyl)-rapamycin.

9. A compound according to claim 1 which is 42-O-(prop-2-enyloxycarbonyl)rapamycin.

10. A compound according to claim 1 which is 42-O-(benzyloxycarbonyl)rapamycin.

11. A method of treating organ and tissue transplant rejection which comprises administration to a warm-blooded animal in need thereof of a therapeutically effective amount of a compound according to the formula:

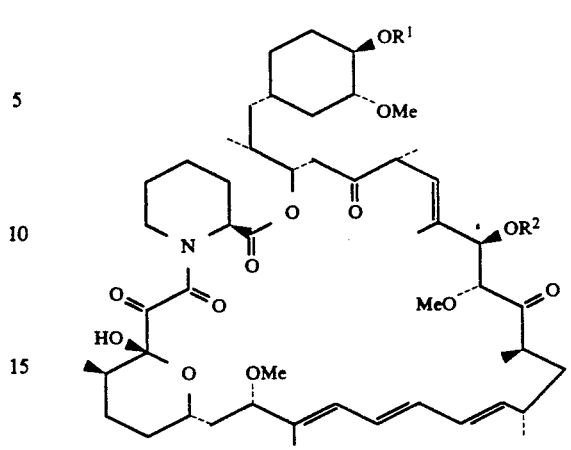

wherein:

R$^1$ and R$^2$ are independently H or —COOR$^3$ but both R$^1$ and R$^2$ cannot be H, and R$^3$ is C$_1$–C$_6$ alkyl where 1 to 3 hydrogens may be replaced by fluorine, chlorine, bromine or iodine, C$_3$–C$_8$ cycloalkyl, C$_2$–C$_6$ alkenyl, or Ar—(CH$_2$-)$_n$—where n is 0 to 6 and Ar is phenyl, phenyl substituted by fluorine, chlorine, bromine, iodine, trifluoromethyl, nitro, cyano, C$_1$–C$_6$ alkyl or C$_1$–C$_6$ alkoxy; pyridinyl, indolyl, quinolyl or furanyl;

or a pharmaceutically acceptable salt thereof.

12. A method of treating autoimmune diseases which comprises administration to a warm-blooded animal in need thereof of a therapeutically effective amount of a compound according to the formula:

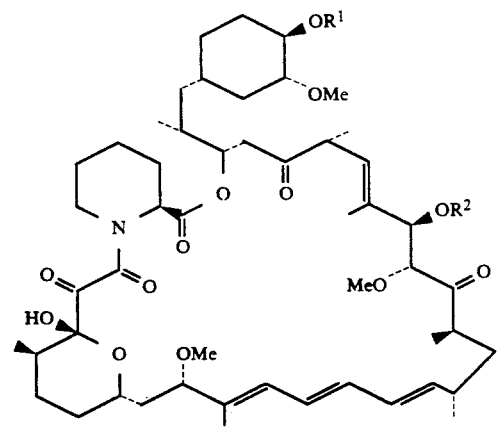

wherein:

R$^1$ and R$^2$ are independently H or —COOR$^3$ but both R$^1$ and R$^2$ cannot be H, and R$^3$ is C$_1$–C$_6$ alkyl where 1 to 3 hydrogens may be replaced by fluorine, chlorine, bromine or iodine, C$_3$–C$_8$ cycloalkyl, C$_2$–C$_6$ alkenyl, or Ar—(CH$_2$-)$_n$—where n is 0 to 6 and Ar is phenyl, phenyl substituted by fluorine, chlorine, bromine, iodine, trifluoromethyl, nitro, cyano, C$_1$–C$_6$ alkyl or C$_1$–C$_6$ alkoxy; pyridinyl, indolyl, quinolyl or furanyl;

or a pharmaceutically acceptable salt thereof.

13. A pharmaceutical composition for the treatment of organ and tissue transplant rejection and autoimmune diseases which comprises a pharmaceutical carrier and an effective amount of a compound having the formula:

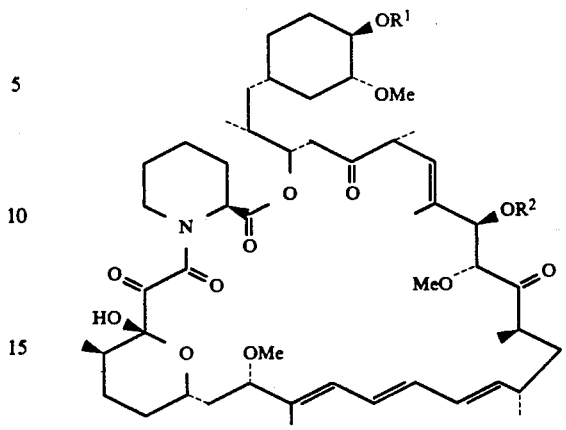

wherein:
$R^1$ and $R^2$ are independently H or $-COOR^3$ but both $R^1$ and $R^2$ cannot be H, and
$R^3$ is $C_1$–$C_6$ alkyl where 1 to 3 hydrogens may be replaced by fluorine, chlorine, bromine or iodine, $C_3$–$C_8$ cycloalkyl, $C_2$–$C_6$ alkenyl, or Ar—$(CH_2)_n$—where n is 0 to 6 and Ar is phenyl, phenyl substituted by fluorine, chlorine, bromine, iodine, trifluoromethyl, nitro, cyano, $C_1$–$C_6$ alkyl or $C_1$–$C_6$ alkoxy; pyridinyl, indolyl, quinolyl or furanyl;
or a pharmaceutically acceptable salt thereof.

* * * * *